US010654768B2

United States Patent
Song et al.

(10) Patent No.: US 10,654,768 B2
(45) Date of Patent: May 19, 2020

(54) METHOD FOR RECOVERING ETHYLBENZENE FROM ALKYLATION PRODUCT OF FLUIDIZED CATALYTIC CRACKING OFF-GAS AND BENZENE

(71) Applicants: SK Innovation Co., Ltd., Seoul (KR); SK Global Chemical Co., Ltd., Seoul (KR)

(72) Inventors: Dae Sung Song, Daejeon (KR); Hee Du Lee, Daejeon (KR); Sang Il Lee, Daejeon (KR); Kyung Jong Oh, Daejeon (KR); Ji Hoon Lee, Daejeon (KR); Yeon Ho Kim, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 15/997,143

(22) Filed: Jun. 4, 2018

(65) Prior Publication Data
US 2018/0362417 A1    Dec. 20, 2018

(30) Foreign Application Priority Data
Jun. 16, 2017   (KR) .................... 10-2017-0076753

(51) Int. Cl.
| C07C 2/66 | (2006.01) |
| C07C 7/11 | (2006.01) |
| C07C 7/04 | (2006.01) |
| C07C 7/00 | (2006.01) |

(52) U.S. Cl.
CPC ............... *C07C 2/66* (2013.01); *C07C 7/005* (2013.01); *C07C 7/04* (2013.01); *C07C 7/11* (2013.01)

(58) Field of Classification Search
None
See application file for complete search history.

(56) References Cited

U.S. PATENT DOCUMENTS

| 5,856,607 A * | 1/1999 | Kim ...................... C07C 15/073 585/314 |
| 7,071,369 B2 | 7/2006 | Pohl |
| 7,795,485 B2 | 9/2010 | Schultz |
| 2004/0167371 A1 * | 8/2004 | Pohl .......................... C07C 2/66 585/449 |
| 2004/0254412 A1 * | 12/2004 | Pohl ....................... B01D 3/009 585/449 |

(Continued)

FOREIGN PATENT DOCUMENTS

| EP | 0726242 A1 | 8/1996 |
| KR | 100415499 B1 | 5/2004 |

(Continued)

*Primary Examiner* — Ali Z Fadhel
(74) *Attorney, Agent, or Firm* — The Webb Law Firm (57) ABSTRACT

The present disclosure provides a process for effectively separating and removing by-products (light gas, C5-C6 hydrocarbon oil fraction, polyethylbenzene) contained in a substantial amount in addition to ethylbenzene as a target compound in an alkylation reaction product of a fluidized catalytic cracking off-gas to prepare ethylbenzene having high purity, and process economical efficiency may be secured by utilizing the polyethylbenzene as an absorbent or gasoline fraction, without requiring a transalkylation reaction for further producing ethylbenzene from polyethylbenzene.

13 Claims, 1 Drawing Sheet

(56) References Cited

U.S. PATENT DOCUMENTS

| | | | |
|---|---|---|---|
| 2004/0254414 A1* | 12/2004 | Hildreth | C07C 2/66 585/648 |
| 2017/0253542 A1* | 9/2017 | Wong | C10G 11/05 |
| 2018/0072640 A1* | 3/2018 | Schwint | C07C 7/11 |

FOREIGN PATENT DOCUMENTS

| | | |
|---|---|---|
| KR | 20060059895 A | 6/2006 |
| KR | 20090042723 A | 4/2009 |

\* cited by examiner

METHOD FOR RECOVERING ETHYLBENZENE FROM ALKYLATION PRODUCT OF FLUIDIZED CATALYTIC CRACKING OFF-GAS AND BENZENE

CROSS-REFERENCE TO RELATED APPLICATION

This application claims priority to Korean Patent Application No. 10-2017-0076753 filed Jun. 16, 2017, the disclosure of which is hereby incorporated in its entirety by reference.

BACKGROUND OF THE INVENTION

Field of the Invention

The present disclosure relates to a method for recovering ethylbenzene from an alkylation product of fluidized catalytic cracking (FCC) off-gas. More specifically, the present disclosure relates to a method for efficiently separating ethylbenzene, a target compound, from other by-products or impurities in an alkylation product of fluidized catalytic cracking (FCC) off-gas and recovering the ethylbenzene having high purity.

Description of Related Art

Ethylbenzene is typically produced through alkylation and transalkylation of ethylene and benzene with high purity. However, efforts have been made to reduce costs due to an increase in ethylene costs, and technology to produce ethylbenzene by utilizing a fluidized catalytic cracking off-gas including a large amount of ethylene has been prominent.

Technology having a purpose similar to the above technology is disclosed in Korean Patent Laid-Open Publication No. 2006-0059895. The technology disclosed in this patent document, a technology for producing ethylbenzene by utilizing a fluidized catalytic cracking off-gas, uses a first alkylation process and a second transalkylation process, recycles a light gas, and uses recycled benzene for an exhaust gas absorption device. Therefore, a recovery rate of benzene and ethylbenzene is low, and further, a reactor may not be easy to operate, since the reactor simultaneously includes a catalyst bed for reaction and distillation.

Meanwhile, Korean Patent Laid-Open Publication No. 2009-0042723 discloses a technology for producing ethylbenzene by separating an ethane/ethylene stream from a fluidized catalytic cracking off-gas. However, the technology of the above patent document is complicated in terms of an overall process and poor in economical efficiency, in that a pretreatment process for separating the ethane/ethylene stream from the fluidized catalytic cracking off-gas is complicated, and an alkylation reactor in a vapor-liquid coexistence state and a transalkylation reactor are used.

SUMMARY OF THE INVENTION

A fluidized catalytic cracking off-gas includes a large amount of ethylene, and also includes a large amount of light gas in addition to ethylene. When ethylbenzene is produced using the fluidized catalytic cracking off-gas, a large amount of ethylene and by-products are included together with ethylbenzene as a reaction product.

Thus, an aspect of the present disclosure may provide a method for recovering desired ethylbenzene having high purity from a reaction product in producing ethylbenzene by utilizing a fluidized catalytic cracking off-gas including a large amount of ethylene and a large amount of light gas.

According to an aspect of the present disclosure, a method for recovering ethylbenzene may include: reacting a mixture of benzene and fluidized catalytic cracking off-gas in an alkylation reactor and flowing the mixture out in a product stream including ethylbenzene; feeding the product stream to a quencher to be separated into a quencher overhead stream, abundant in a light gas, and a quencher bottom stream, abundant in a heavy oil fraction; feeding the quencher bottom stream to a benzene recovery column to be separated into a benzene recovery column overhead liquid stream, abundant in unreacted benzene and a C5-C6 hydrocarbon oil fraction, a benzene recovery column overhead vapor stream, abundant in a light gas, and a benzene recovery column bottom stream, abundant in a heavy oil fraction; and feeding the benzene recovery column bottom stream to an ethylbenzene recovery column and recovering ethylbenzene.

The method may further include: raising a temperature of the benzene or the mixture of benzene and fluidized catalytic cracking off-gas by heat exchange with the product stream.

The mixture of benzene and fluidized catalytic cracking off-gas may be heated and fed to the alkylation reactor.

The method may further include: feeding the quencher overhead stream to an absorption tower, absorbing the heavy oil fraction by an absorbent to be recovered to an absorption tower bottom stream, and mixing with the quencher bottom stream.

The light gas in the quencher overhead stream may be recovered to an absorption tower overhead stream.

The quencher bottom stream may be fed to an absorbent recovery column to be separated into a side-cut stream abundant in benzene and an absorbent recovery column bottom stream, abundant in a heavy oil fraction, and the side-cut stream may be mixed with the quencher bottom stream.

At least a portion of the absorbent recovery column bottom stream may be fed to the absorption tower as an absorbent.

The light gas included in the quencher bottom stream fed to the absorbent recovery column may be separated into an absorbent recovery column overhead stream and recovered.

The benzene recovery column overhead liquid stream may be recycled to the alkylation reactor.

The benzene recovery column overhead vapor stream may be fed to the absorption tower to absorb benzene with the absorbent, and the absorption tower bottom stream containing the benzene separated from the light gas may be discharged from the absorption tower and mixed with the quencher bottom stream.

The benzene recovery column overhead vapor stream may be fed to the absorption tower.

A residue may be discharged into an ethylbenzene recovery column bottom stream after recovering the ethylbenzene in the ethylbenzene recovery column, and at least a portion of the ethylbenzene recovery column bottom stream may be fed to the absorption tower as the absorbent.

A residue may be discharged into an ethylbenzene recovery column bottom stream after recovering the ethylbenzene in the ethylbenzene recovery column, the ethylbenzene recovery column bottom stream may be mixed with the absorbent recovery column bottom stream, and at least a portion of a heavy oil fraction stream in which the ethylbenzene recovery column bottom stream and the absorbent recovery column bottom stream are mixed may be fed to the absorption tower as the absorbent.

A portion of the heavy oil fraction may be separated and used as a gasoline fuel.

The light gas may be used as a fuel.

BRIEF DESCRIPTION OF THE DRAWING

The above and other aspects, features and other advantages of the present disclosure will be more clearly understood from the following detailed description taken in conjunction with the accompanying drawing, in which:

the FIGURE schematically illustrates an exemplary embodiment in the present disclosure.

DESCRIPTION OF THE INVENTION

Figure 1:
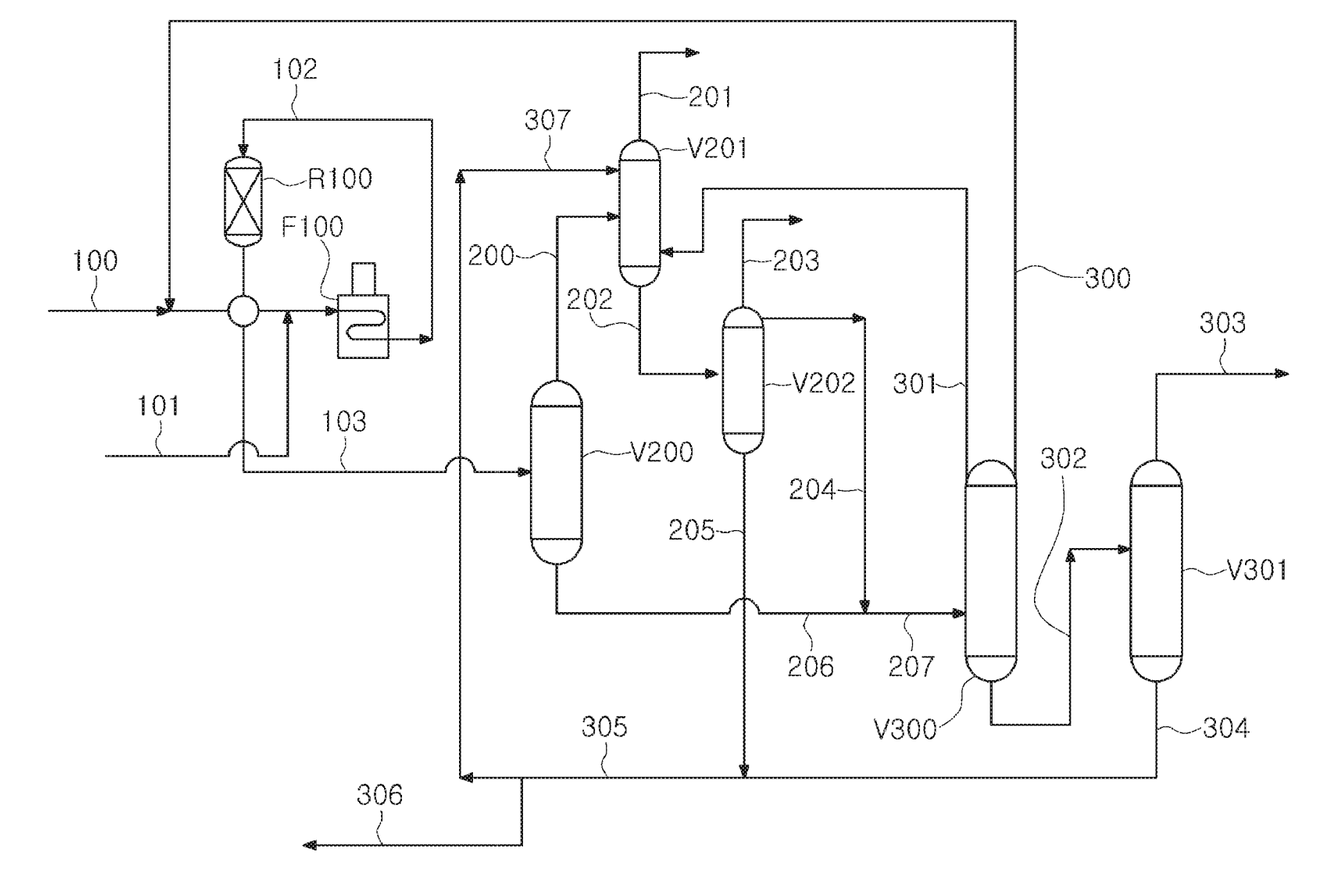

Hereinafter, exemplary embodiments in the present disclosure will be described in detail with reference to the accompanying FIGURE. The FIGURE is a schematic view illustrating an example of a method for recovering ethylbenzene from an alkylation product of benzene and a fluidized catalytic cracking off-gas according to the present disclosure.

According to an exemplary embodiment in the present disclosure, as shown in the FIGURE, the method may include reacting a mixture of benzene and a fluidized catalytic cracking off-gas 101 in an alkylation reactor R100. Since the fluidized catalytic cracking off-gas 101 includes a large amount of ethylene, ethylbenzene may be produced by a reaction of ethylene of the fluidized catalytic cracking off-gas 101 and benzene in the alkylation reactor R100. Here, the benzene may be fed as separate benzene (100), and the benzene that does not react with ethylene in a process of the present disclosure may be recovered, recycled, and fed to the alkylation reactor R100.

A mixture stream 102 in which the benzene 100 and the fluidized catalytic cracking off-gas 101 were mixed fed to the alkylation reactor R100 may be heated and fed to the alkylation reactor R100. The mixture stream may be heated to a temperature range in which an alkylation reaction is capable of being generated, for example, 300 to 500° C. A difference between the upper limit and the lower limit of the temperature may vary depending on a catalyst used, but the temperature may be 300° C. or higher for generating an efficient reaction. Meanwhile, considering that the alkylation reaction is an exothermic reaction and an ignition temperature of ethylene is 543° C., the temperature may be 500° C. or lower.

Ethylbenzene is produced by the reaction of benzene and ethylene included in the mixture stream 102 by the alkylation reaction in the alkylation reactor R100. For this reaction, conditions of the alkylation reactor (R100) are not particularly limited, but may be a pressure of 10 to 20 kgf, a temperature of 300 to 500° C., and a reaction condition of 0.5 to 5 kg/hr$_{ethylene}$/kg$_{catalyst}$.

The product produced by the alkylation reaction flows out from the alkylation reactor R100 as a product stream 103 including ethylbenzene. The product stream 103 may be heat exchanged with benzene 100 fed as a reactant. Through the heat exchange, the product stream 103 may be cooled and the reactant fed to the alkylation reactor R100 may be preheated. The heat exchange may be performed on the mixture stream 102 including the benzene 100 and the fluidized catalytic cracking off-gas 101, if necessary.

The product stream 103 flowing out from the alkylation reactor R100 includes a light gas, a C5-C6 hydrocarbon, and a heavy oil fraction including benzene or higher, and in order to recover benzene, ethylbenzene, polyethylbenzene, etc., from the product stream, the product stream 103 is introduced into a quencher V200.

In the quencher V200, a quencher bottom stream 206 abundant in heavy oil fraction may be recovered by lowering a temperature of the heavy oil fraction including benzene or higher in the product stream 103 by pump-around. Here, a recovery rate of the heavy oil fraction may be adjusted by regulating an amount of the heavy oil fraction to be processed by the pump around.

The quencher bottom stream 206 may be separated into a heavy oil fraction including ethylbenzene and benzene through a benzene recovery column V300 to recover ethylbenzene from the heavy oil fraction including ethylbenzene. This will be described below.

A residue after the heavy oil fraction is recovered to the quencher bottom stream 206 is abundant in the light gas, and may be recovered to the quencher overhead stream 200. Since the quencher overhead stream 200 includes a portion of the heavy oil fraction including benzene or higher, the quencher overhead stream 200 may be introduced into an absorption tower V201 to recover the heavy oil fraction from the quencher overhead stream 200.

The absorption tower V201 into which the quencher overhead stream 200 is introduced may include an absorbent for absorbing the heavy oil fraction included in the quencher overhead stream 200. The absorbent may be any commonly used absorbent for absorption of the heavy oil fragment. However, the absorption may be performed by utilizing the heavy oil fraction including ethylbenzene or higher produced after the reaction according to the method of the present disclosure, thereby increasing process economical efficiency. The heavy oil fraction that is usable as the absorbent may be, for example, an absorbent recovery column bottom stream 205 or an ethylbenzene recovery column bottom stream 304 composed of almost 100% heavy oil fraction, and these streams 205 and 304 may be mixed and used as a heavy oil fraction stream 305.

By operating the absorption tower V201 using the heavy oil fraction stream 305, the heavy oil fraction including benzene or higher may be absorbed from the quencher overhead stream 200 fed to the absorption tower V201, and may be recovered to an absorption tower bottom stream 202.

Further, an absorption tower overhead stream 201 abundant in light gas may be recovered from an upper part of the absorption tower V201, and this absorption tower overhead stream 201 may be used as a fuel gas.

The absorption tower bottom stream 202 may be fed to the benzene recovery column V300 to be separated into the benzene and the heavy oil fraction, and the absorbent may be removed in view of reducing burden on the benzene recovery column V300. Thus, the absorption tower bottom stream 202 may be fed to the absorbent recovery column V202 for recovery of the absorbent.

The absorption tower bottom stream 202 may include the light gas and the C5-C6 hydrocarbon oil fraction together with the heavy oil fraction, the light gas and the C5-C6 hydrocarbon oil fraction may be removed by the absorbent recovery column overhead stream 203, and the heavy oil fraction including ethylbenzene or higher used as the absorbent may be recovered to the absorbent recovery column bottom stream 205 and recycled to the absorption tower V201 as the absorbent. Here, the benzene may be recovered into a side-cut stream 204 of the absorbent recovery column V202.

Meanwhile, the quencher bottom stream 206 and the side-cut stream 204 of the absorbent recovery column V202 include a large amount of unreacted benzene and heavy oil fraction as the reaction product including benzene or higher such as ethylbenzene, or the like. From these streams, unreacted benzene, ethylbenzene, and heavy oil fraction including ethylbenzene or higher may be separated and recovered, respectively.

First, the quencher bottom stream 206 alone or the quencher bottom stream 206 and the side-cut stream 204 may be mixed and fed to the benzene recovery column V300. Thus, the unreacted benzene may be separated and recovered from the heavy oil fraction including benzene or higher. The unreacted benzene may be separated into an overhead liquid stream of the benzene recovery column, and simultaneously, the light gas included in the stream fed to the benzene recovery column may be separated into a benzene recovery column overhead vapor stream.

The unreacted benzene separated into the benzene recovery column overhead liquid stream may be recycled to the alkylation reactor R100 as a reactant of the alkylation reaction and may be reacted with the fluidized catalytic cracking off-gas 101 to produce ethylbenzene.

Meanwhile, in the benzene recovery column (V300), a trace amount of light gas present in the benzene mixture stream 207 may be separated and recovered to the benzene recovery column overhead vapor stream 301. The light gas may be utilized as a fuel gas as described above. However, since the vapor stream may include a trace amount of the heavy oil fraction such as benzene, or the like, the vapor stream may be recycled to the absorption tower V201 for recovery of the heavy oil fraction to recover benzene included in a trace amount to the absorption tower bottom stream 202 while removing the light gas together to the absorption tower overhead stream 201.

Further, a benzene residue stream 302 remaining after recovering the benzene in the benzene recovery column V300 may be discharged to a benzene recovery column bottom stream. The benzene residue stream 302 includes the heavy oil fraction including ethylbenzene or higher, and from the benzene residue stream, desired ethylbenzene may be recovered.

The benzene residue stream 302 may be fed to an ethylbenzene recovery column V301 to recover a final target product, ethylbenzene. The target product, ethylbenzene 303 may be recovered through an upper part of the ethylbenzene recovery column V301, and the heavy oil fraction including ethylbenzene or higher may be discharged to the ethylbenzene recovery column bottom stream 304.

As described above, the ethylbenzene recovery column bottom stream 304 may be mostly composed of the heavy oil fraction that is usable as the absorbent in the absorption tower V201, thereby being recycled to the absorption tower. Here, the ethylbenzene recovery column bottom stream 304 may be mixed with the absorbent recovery column bottom stream 205 from the absorbent recovery column V202 and may be fed to the absorption tower V201 as the heavy oil fraction stream 305 for being used as the absorbent.

Here, the ethylbenzene recovery column bottom stream 304, the absorbent recovery column bottom stream 205 or the heavy oil fraction stream 305 may be cooled and fed to the absorption tower V201 before being fed to the absorption tower V201. Further, these streams 205, 304, and 305 in an amount exceeding required as the absorbent may be transported to a gasoline pool 306 and used as a gasoline fuel.

According to the present disclosure as described above, ethylbenzene having high purity may be prepared by effectively separating and removing by-products such as light gas, C5-C6 hydrocarbon oil fraction, polyethylbenzene, and the like, contained in a substantial amount in addition to ethylbenzene as the target compound in the alkylation reaction product of the fluidized catalytic cracking off-gas without using ethylene having high purity. Further, the fluidized catalytic cracking off-gas, which is not applicable in the conventional process using the ethylene with high purity, may be used.

Example

Hereinafter, the present disclosure will be described in detail. The following Example is described for illustrative purposes only and is not to be construed as limiting the scope of the present disclosure.

The present Example is described with reference to the FIGURE.

A supplemental benzene 100 having a composition shown in Table 3 and a recycled benzene 300 having a composition shown in Table 4 were mixed to form a mixed benzene, and then mixed with a fluidized catalytic cracking off-gas 101 having a composition of Table 3. A mixture stream 102 in which the mixed benzene and the fluidized catalytic cracking off-gas 101 were mixed had a composition as shown in Table 3, and was fed to an alkylation reactor R100 to perform an alkylation reaction, and flowed out to a product stream 103.

Here, the mixed benzene was heat-exchanged with the product stream 103 and then mixed with the fluidized catalytic cracking off-gas 101. The mixture stream 102 was heated under alkylation reaction operating conditions (about 17 kgf and about 390° C.) by a heating furnace F100 and fed to the alkylation reactor R100.

The alkylation reactor R100 was operated under the operating conditions shown in Table 1 on the next page.

TABLE 1

| Alkylation Reactor Type | Alkylation Reactor Inlet Temperature | Alkylation Reactor Inlet Pressure | Weight Hourly Space Velocity (WHSV) in relation to ethylene | Benzene/Ethylene Mass Ratio | Conversion Ratio |
|---|---|---|---|---|---|
| Fixed Bed Reactor | 390° C. | 17.3 kg/cm² g | 2 hr$^{-1}$ | 18 | 100% |

A composition of the thus-obtained product stream 103 was analyzed, and results thereof are shown in Table 3.

As could be appreciated from Table 3, the product stream 103 included 15.6 wt % light gas, 0.2 wt % C5-C6 hydrocarbon oil fraction, and 84.2 wt % heavy oil fraction including benzene or higher such as benzene, ethylbenzene, polyethylbenzene, or the like. Thus, it could be appreciated that in the alkylation reactor R100, benzene in the mixture stream 102 was alkylated with a C2-C3 hydrocarbon oil fraction such as ethylene, or the like, in the fluidized catalytic cracking off-gas 101 to produce ethylbenzene.

The product stream 103 was in a high temperature state at 160° C. including the light gas together with the heavy oil fraction including benzene or higher, and fed to a quencher V200 set under the operating conditions shown in Table 2 to recover the heavy oil fraction from the product stream 103.

In the quencher V200, the heavy oil fraction including benzene or higher was subjected to pump-around in the product stream 103 to lower the temperature, such that the heavy oil fraction including benzene or higher was recovered to a quencher bottom stream 206 including 99.3% by weight or more of the heavy oil fraction including benzene or higher, and the light gas was removed to a quencher overhead stream 200. The compositions of the recovered quencher bottom stream 206 and the quencher overhead stream 200 were analyzed and results thereof are shown in Table 3, respectively.

As could be appreciated from Table 3, most of the heavy oil fraction in the product stream 103 could be recovered to the quencher bottom stream 206, but the quencher overhead stream 200 abundant in the light gas still included about 9 wt % of the heavy oil fraction including benzene or higher. Thus, in order to further recover the heavy oil fraction in the quencher overhead stream 200, the quencher overhead stream 200 was introduced into the absorption tower V201.

In the absorption tower V201, an absorbent recovery column bottom stream 205 obtained in the process as the absorbent of the heavy oil fraction and an ethylbenzene recovery column bottom stream 304 were mixed and used. Here, operating conditions of the absorption tower V201 were set as shown in Table 2 below.

From the quencher overhead stream 200, the heavy oil fraction including benzene or higher were recovered to the absorption tower bottom stream 202 by the absorption tower V201, and a composition thereof was analyzed and shown in Table 3 below. As could be appreciated from Table 3, 99% or more of the heavy oil fraction included in the quencher overhead stream 200 introduced into the absorption tower V201 was recovered to the absorption tower bottom stream 202.

Meanwhile, since the absorption tower overhead stream 201 recovered from the upper part of the absorption tower V201 abundantly included the light gas as shown in Table 3, the absorption tower overhead stream 201 could be used as a fuel gas.

It could be appreciated from Table 3 that the absorption tower bottom stream 202 included a portion of the light gas, such that the absorption tower bottom stream 202 was fed to an absorbent recovery column V202. The absorbent recovery column V202 was operated under operating conditions shown in Table 2 below.

The absorbent recovery column V202 was separated into a side-cut stream 204, an absorbent recovery column overhead stream 203, and an absorbent recovery column bottom stream 205. A compositional component of each of these streams was analyzed, and results thereof are shown in Table 3.

As could be appreciated from Table 3, the absorbent recovery column overhead stream 203 was mostly composed of the light gas, and the side-cut stream 204 included about 49% of benzene and the heavy oil fraction above benzene, and almost 100% of the absorbent recovery column bottom stream 205 included the heavy oil fraction including benzene or higher.

Thus, the absorbent recovery column bottom stream 205 was recycled to the absorption tower for being used as the absorbent, and the side-cut stream 204 was fed to a benzene recovery column V300 together with the quencher bottom stream 206. The benzene recovery column V300 was operated under operating conditions shown in Table 2 below.

From the benzene recovery column V300, a trace amount of light gas included in the benzene mixture stream was separated to a benzene recovery column overhead vapor stream 301. Here, the benzene recovery column overhead vapor stream 301 included a portion of benzene as shown in Table 4, such that in order to recover benzene, the benzene recovery column overhead vapor stream was recycled to the absorption tower V201 to absorb benzene as the absorbent, and the light gas was removed to the absorption tower overhead stream 201.

Meanwhile, unreacted benzene in the benzene recovery column V300 was recovered to a benzene recovery column overhead liquid stream 300, and a composition thereof was analyzed. As could be appreciated from FIG. 3, 98% by weight or more of the benzene recovery column overhead liquid stream 300 was benzene, and then recycled and mixed with the fluidized catalytic cracking off-gas 101 and fed to the alkylation reactor R100.

Further, the benzene recovery column bottom stream 302 was recovered, and composition components thereof were analyzed and shown in Table 4 below. As could be appreciated from Table 4, the benzene recovery column bottom stream 302 included ethylbenzene and the heavy oil fraction above ethylbenzene, such that in order to recover the ethylbenzene from this, the benzene recovery column bottom stream was fed to an ethylbenzene recovery column V301.

The ethylbenzene recovery column V301 was operated under operating conditions shown in Table 2 below.

Ethylbenzene 303 was recovered from the overhead stream of the ethylbenzene recovery column V301, and the heavy oil fraction including ethylbenzene or higher was recovered to the ethylbenzene recovery column bottom stream 304. A composition of each of the recovered ethylbenzene 303 and ethylbenzene recovery column bottom stream 304 was analyzed, and results thereof are shown in Table 4 below.

As could be appreciated from Table 4, an overhead stream of the ethylbenzene recovery column 303 included 99% or more of the ethylbenzene produced in the alkylation reactor, and an alkylation reaction product was recovered in a yield of almost 99%.

Meanwhile, it could be appreciated from Table 4 that almost 100% of the ethylbenzene recovery column bottom stream 304 included a heavy oil fraction including ethylbenzene or higher, such that the ethylbenzene recovery column bottom stream 304 could be used as an absorbent for the absorption tower V201. Thus, the ethylbenzene recovery column bottom stream 304 was recycled to the absorption tower V201. Here, the ethylbenzene recovery column bottom stream 304 was combined with the absorbent recovery column bottom stream 205 from the absorbent recovery column V202, cooled, and fed to the absorption tower in an amount required as the absorbent, and the remainder was fed to a gasoline pool 306.

TABLE 2

|  | Quencher (V200) | Absorption Tower (V201) | Absorbent Recovery Column (V202) | Benzene Recovery Column (V300) | Ethylbenzene Recovery Column (V301) |
|---|---|---|---|---|---|
| Tower Top Pressure [kg/cm² g] | 11.5 | 10.9 | 5 | 11 | 5.5 |
| Tower Top Temperature [° C.] | 40 | 60 | 40 | 152 | 222 |
| Tower Low Temperature [° C.] | 139 | 50 | 258 | 269 | 260 |
| Theoretical Plate Number | 10 | 30 | 50 | 40 | 56 |
| Reflux Ratio | — | — | 2.06 | 0.56 | 0.56 |

TABLE 3

|  | 100 | 101 | 102 | 103 | 200 | 201 | 202 | 203 | 204 | 205 | 206 | 207 |
|---|---|---|---|---|---|---|---|---|---|---|---|---|
| Temperature C. | 15 | 120 | 389 | 160 | 39.9 | 59.8 | 50.1 | 39.7 | 178.8 | 258.1 | 139 | 140.9 |
| Pressure kg/sqcmg | 18.1 | 18.1 | 17.3 | 12.2 | 11.5 | 10.9 | 10.9 | 5.0 | 5.4 | 5.4 | 11.5 | 11.5 |
| Vapor Frac | 0 | 1 | 1 | 0.856 | 1 | 1 | 0 | 1 | 0 | 0 | 0 | 0 |
| Mass Flow kg/hr | 27354 | 43183 | 204939 | 204983 | 33966 | 31710 | 19245 | 266 | 8130 | 10849 | 171023 | 179153 |
| Mass Flow kg/hr |  |  |  |  |  |  |  |  |  |  |  |  |
| H2 | 0.0 | 1277.1 | 1277.1 | 1277.1 | 1271.0 | 1274.4 | 0.6 | 0.6 | 0.0 | 0.0 | 6.1 | 6.1 |
| CO2 | 0.0 | 1928.9 | 1928.9 | 1928.9 | 1847.9 | 1850.7 | 26.4 | 26.4 | 0.0 | 0.0 | 81.0 | 81.0 |
| CO | 0.0 | 2045.8 | 2045.8 | 2045.8 | 2027.0 | 2035.0 | 2.5 | 2.5 | 0.0 | 0.0 | 18.8 | 18.8 |
| O2 | 0.0 | 141.4 | 141.4 | 141.4 | 139.3 | 140.2 | 0.3 | 0.3 | 0.0 | 0.0 | 2.1 | 2.1 |
| N2 | 0.0 | 9462.2 | 9462.2 | 9462.2 | 9386.1 | 9421.5 | 10.8 | 10.8 | 0.0 | 0.0 | 76.1 | 76.1 |
| C1 | 0.0 | 9357.7 | 9357.7 | 9357.7 | 9171.4 | 9215.9 | 33.1 | 33.1 | 0.0 | 0.0 | 186.2 | 186.2 |
| C2 | 0.0 | 7117.1 | 7117.1 | 7117.1 | 6700.0 | 6686.2 | 122.3 | 12.3 | 0.0 | 0.0 | 417.1 | 417.1 |
| C2= | 0.0 | 8939.5 | 893.5 | 0.0 | 0.0 | 0.0 | 0.0 | 0.0 | 0.0 | 0.0 | 0.0 | 0.0 |
| C3 | 0.0 | 338.2 | 338.2 | 338.2 | 270.1 | 265.2 | 15.3 | 15.3 | 0.0 | 0.0 | 68.1 | 68.1 |
| C3= | 0.0 | 1781.3 | 1781.3 | 0.0 | 0.0 | 0.0 | 0.0 | 0.0 | 0.0 | 0.0 | 0.0 | 0.0 |
| IC4 | 0.0 | 243.9 | 243.9 | 243.9 | 91.8 | 89.3 | 11.5 | 11.5 | 0.0 | 0.0 | 152.1 | 152.1 |
| NC4 | 0.0 | 71.8 | 71.8 | 71.8 | 20.4 | 20.0 | 3.7 | 3.7 | 0.0 | 0.0 | 51.3 | 51.3 |
| TB2 | 0.0 | 59.5 | 59.5 | 0.0 | 0.0 | 0.0 | 0.0 | 0.0 | 0.0 | 0.0 | 0.0 | 0.0 |
| B-1 | 0.0 | 41.0 | 41.0 | 0.0 | 0.0 | 0.0 | 0.0 | 0.0 | 0.0 | 0.0 | 0.0 | 0.0 |
| IC4= | 0.0 | 65.6 | 65.6 | 0.0 | 0.0 | 0.0 | 0.0 | 0.0 | 0.0 | 0.0 | 0.0 | 0.0 |
| CB2 | 0.0 | 45.1 | 45.1 | 0.0 | 0.0 | 0.0 | 0.0 | 0.0 | 0.0 | 0.0 | 0.0 | 0.0 |
| IC5 | 0.0 | 106.6 | 106.6 | 106.6 | 16.4 | 12.6 | 6.0 | 6.0 | 0.0 | 0.0 | 90.2 | 90.2 |
| NC5 | 0.0 | 8.2 | 8.2 | 8.2 | 1.2 | 0.9 | 0.5 | 0.5 | 0.0 | 0.0 | 7.0 | 7.0 |
| C5-OLE | 0.0 | 47.2 | 47.2 | 0.0 | 0.0 | 0.0 | 0.0 | 0.0 | 0.0 | 0.0 | 0.0 | 0.0 |
| C6-HEA | 0.0 | 104.5 | 104.5 | 104.5 | 5.4 | 1.6 | 5.4 | 5.4 | 0.0 | 0.0 | 99.2 | 99.2 |
| BZ | 27354.2 | 0.0 | 161806.5 | 134995.6 | 2917.6 | 14.6 | 3975.6 | 27.2 | 3943.8 | 4.6 | 131578.0 | 135521.8 |
| TOL | 0.0 | 0.0 | 0.0 | 848.7 | 6.1 | 0.2 | 9.6 | 0.0 | 8.4 | 1.2 | 842.6 | 851.0 |
| EB | 0.0 | 0.0 | 0.0 | 29014.2 | 85.2 | 6.8 | 136.4 | 0.0 | 55.7 | 80.7 | 28929.1 | 28984.8 |
| IPB | 0.0 | 0.0 | 0.0 | 5085.8 | 8.6 | 596.4 | 8406.9 | 0.0 | 2538.6 | 5868.0 | 5077.1 | 7616.0 |
| DEB | 0.0 | 0.0 | 0.0 | 2738.7 | 0.6 | 58.1 | 5329.2 | 0.0 | 1294.2 | 4035.0 | 2738.0 | 4032.2 |
| BUTYLBZ | 0.0 | 0.0 | 0.0 | 502.2 | 0.2 | 19.2 | 951.7 | 0.0 | 241.7 | 710.1 | 502.0 | 743.6 |
| PENTYLBZ | 0.0 | 0.0 | 0.0 | 100.4 | 0.0 | 1.6 | 197.0 | 0.0 | 47.4 | 149.6 | 100.4 | 147.8 |
| WATER | 0.0 | 0.0 | 0.0 | 0.0 | 0.0 | 0.0 | 0.0 | 0.0 | 0.0 | 0.0 | 0.0 | 0.0 |
| Mass Frac |  |  |  |  |  |  |  |  |  |  |  |  |
| H2 | 0.000 | 0.030 | 0.006 | 0.006 | 0.037 | 0.040 | 0.000 | 0.002 | 0.000 | 0.000 | 0.000 | 0.000 |
| CO2 | 0.000 | 0.045 | 0.009 | 0.009 | 0.054 | 0.058 | 0.001 | 0.099 | 0.000 | 0.000 | 0.000 | 0.000 |
| CO | 0.000 | 0.047 | 0.010 | 0.010 | 0.060 | 0.064 | 0.000 | 0.009 | 0.000 | 0.000 | 0.000 | 0.000 |
| O2 | 0.000 | 0.008 | 0.001 | 0.001 | 0.004 | 0.004 | 0.000 | 0.001 | 0.000 | 0.000 | 0.000 | 0.000 |
| N2 | 0.000 | 0.219 | 0.046 | 0.046 | 0.276 | 0.297 | 0.001 | 0.041 | 0.000 | 0.000 | 0.000 | 0.000 |
| C1 | 0.000 | 0.217 | 0.046 | 0.046 | 0.270 | 0.291 | 0.002 | 0.125 | 0.000 | 0.000 | 0.000 | 0.000 |
| C2 | 0.000 | 0.165 | 0.035 | 0.035 | 0.197 | 0.211 | 0.006 | 0.461 | 0.000 | 0.000 | 0.000 | 0.000 |
| C2= | 0.000 | 0.207 | 0.044 | 0.000 | 0.000 | 0.000 | 0.000 | 0.000 | 0.000 | 0.000 | 0.000 | 0.000 |
| C3 | 0.000 | 0.008 | 0.002 | 0.002 | 0.008 | 0.008 | 0.001 | 0.058 | 0.000 | 0.000 | 0.000 | 0.000 |
| C3= | 0.000 | 0.041 | 0.009 | 0.000 | 0.000 | 0.000 | 0.000 | 0.000 | 0.000 | 0.000 | 0.000 | 0.000 |
| IC4 | 0.000 | 0.006 | 0.001 | 0.001 | 0.003 | 0.003 | 0.001 | 0.043 | 0.000 | 0.000 | 0.001 | 0.001 |
| NC4 | 0.000 | 0.002 | 0.000 | 0.000 | 0.001 | 0.001 | 0.000 | 0.014 | 0.000 | 0.000 | 0.000 | 0.000 |
| TB2 | 0.000 | 0.001 | 0.000 | 0.000 | 0.000 | 0.000 | 0.000 | 0.000 | 0.000 | 0.000 | 0.000 | 0.000 |
| B-1 | 0.000 | 0.001 | 0.000 | 0.000 | 0.000 | 0.000 | 0.000 | 0.000 | 0.000 | 0.000 | 0.000 | 0.000 |
| IC4= | 0.000 | 0.002 | 0.000 | 0.000 | 0.000 | 0.000 | 0.000 | 0.000 | 0.000 | 0.000 | 0.000 | 0.000 |
| CB2 | 0.000 | 0.001 | 0.000 | 0.000 | 0.000 | 0.000 | 0.000 | 0.000 | 0.000 | 0.000 | 0.000 | 0.000 |
| IC5 | 0.000 | 0.002 | 0.001 | 0.001 | 0.000 | 0.000 | 0.000 | 0.023 | 0.000 | 0.000 | 0.001 | 0.001 |
| NC5 | 0.000 | 0.000 | 0.000 | 0.000 | 0.000 | 0.000 | 0.000 | 0.002 | 0.000 | 0.000 | 0.000 | 0.000 |
| C5-OLE | 0.000 | 0.001 | 0.000 | 0.000 | 0.000 | 0.000 | 0.000 | 0.000 | 0.000 | 0.000 | 0.000 | 0.000 |

TABLE 3-continued

| | | | | | | | | | | | | |
|---|---|---|---|---|---|---|---|---|---|---|---|---|
| C6-HEA | 0.000 | 0.002 | 0.001 | 0.001 | 0.000 | 0.000 | 0.000 | 0.020 | 0.000 | 0.000 | 0.001 | 0.001 |
| BZ | 1.000 | 0.000 | 0.789 | 0.656 | 0.086 | 0.000 | 0.207 | 0.102 | 0.485 | 0.000 | 0.769 | 0.756 |
| TOL | 0.000 | 0.000 | 0.000 | 0.004 | 0.000 | 0.000 | 0.000 | 0.001 | 0.000 | 0.005 | 0.005 |
| EB | 0.000 | 0.000 | 0.000 | 0.142 | 0.003 | 0.000 | 0.007 | 0.000 | 0.007 | 0.007 | 0.169 | 0.162 |
| IPB | 0.000 | 0.000 | 0.000 | 0.025 | 0.000 | 0.019 | 0.437 | 0.000 | 0.312 | 0.541 | 0.030 | 0.043 |
| DEB | 0.000 | 0.000 | 0.000 | 0.013 | 0.000 | 0.002 | 0.277 | 0.000 | 0.159 | 0.372 | 0.016 | 0.023 |
| BUTYLBZ | 0.000 | 0.000 | 0.000 | 0.002 | 0.000 | 0.001 | 0.049 | 0.000 | 0.030 | 0.065 | 0.003 | 0.004 |
| PENTYLBZ | 0.000 | 0.000 | 0.000 | 0.000 | 0.000 | 0.000 | 0.010 | 0.000 | 0.006 | 0.014 | 0.001 | 0.001 |
| WATER | 0.000 | 0.000 | 0.000 | 0.000 | 0.000 | 0.000 | 0.000 | 0.000 | 0.000 | 0.000 | 0.000 | 0.000 |

TABLE 4

| | 300 | 301 | 302 | 303 | 304 | 305 | 308 | 307 |
|---|---|---|---|---|---|---|---|---|
| Temperature C. | 151.7 | 151.7 | 269.2 | 40 | 260 | 40 | 40 | 40.5 |
| Pressure kg/sqcmg | 11.0 | 11.0 | 11.3 | 5.0 | 5.9 | 4.9 | 4.9 | 12.0 |
| Vapor Frac | 0 | 1 | 0 | 0 | 0 | 0 | 0 | 0 |
| Mass Flaw kg/hr | 136265 | 1376 | 41511 | 28977 | 12534 | 23383 | 7770 | 15613 |
| Mass Flow kg/hr | | | | | | | | |
| H2 | 2.1 | 4.0 | 0.0 | 0.0 | 0.0 | 0.0 | 0.0 | 0.0 |
| CO2 | 51.8 | 29.3 | 0.0 | 0.0 | 0.0 | 0.0 | 0.0 | 0.0 |
| CO | 8.3 | 10.5 | 0.0 | 0.0 | 0.0 | 0.0 | 0.0 | 0.0 |
| O2 | 0.9 | 1.2 | 0.0 | 0.0 | 0.0 | 0.0 | 0.0 | 0.0 |
| N2 | 29.9 | 46.2 | 0.0 | 0.0 | 0.0 | 0.0 | 0.0 | 0.0 |
| C1 | 108.6 | 77.7 | 0.0 | 0.0 | 0.0 | 0.0 | 0.0 | 0.0 |
| C2 | 308.6 | 108.5 | 0.0 | 0.0 | 0.0 | 0.0 | 0.0 | 0.0 |
| C2= | 0.0 | 0.0 | 0.0 | 0.0 | 0.0 | 0.0 | 0.0 | 0.0 |
| C3 | 57.7 | 10.4 | 0.0 | 0.0 | 0.0 | 0.0 | 0.0 | 0.0 |
| C3= | 0.0 | 0.0 | 0.0 | 0.0 | 0.0 | 0.0 | 0.0 | 0.0 |
| IC4 | 143.1 | 9.0 | 0.0 | 0.0 | 0.0 | 0.0 | 0.0 | 0.0 |
| NC4 | 48.1 | 3.2 | 0.0 | 0.0 | 0.0 | 0.0 | 0.0 | 0.0 |
| TB2 | 0.0 | 0.0 | 0.0 | 0.0 | 0.0 | 0.0 | 0.0 | 0.0 |
| B-1 | 0.0 | 0.0 | 0.0 | 0.0 | 0.0 | 0.0 | 0.0 | 0.0 |
| IC4= | 0.0 | 0.0 | 0.0 | 0.0 | 0.0 | 0.0 | 0.0 | 0.0 |
| CB2 | 0.0 | 0.0 | 0.0 | 0.0 | 0.0 | 0.0 | 0.0 | 0.0 |
| IC5 | 88.0 | 2.2 | 0.0 | 0.0 | 0.0 | 0.0 | 0.0 | 0.0 |
| NC5 | 6.8 | 0.2 | 0.0 | 0.0 | 0.0 | 0.0 | 0.0 | 0.0 |
| C5-OLE | 0.0 | 0.0 | 0.0 | 0.0 | 0.0 | 0.0 | 0.0 | 0.0 |
| C6-HEA | 97.6 | 1.6 | 0.0 | 0.0 | 0.0 | 0.0 | 0.0 | 0.0 |
| BZ | 134452.3 | 1069.5 | 0.0 | 0.0 | 0.0 | 4.6 | 1.5 | 3.1 |
| TOL | 847.9 | 2.9 | 0.2 | 0.0 | 0.0 | 1.2 | 0.4 | 0.8 |
| EB | 13.6 | 0.0 | 28971.1 | 28964.8 | 6.3 | 87.0 | 28.9 | 58.1 |
| IPB | 0.0 | 0.0 | 7615.9 | 12.3 | 7603.7 | 13471.7 | 4476.8 | 8995.2 |
| DEB | 0.0 | 0.0 | 4032.2 | 0.0 | 4032.2 | 8067.2 | 2680.8 | 5386.5 |
| BUTYLBZ | 0.0 | 0.0 | 743.6 | 0.0 | 743.6 | 1453.7 | 483.1 | 970.7 |
| PENTYLBZ | 0.0 | 0.0 | 147.8 | 0.0 | 147.8 | 297.4 | 98.8 | 198.6 |
| WATER | 0.0 | 0.0 | 0.0 | 0.0 | 0.0 | 0.0 | 0.0 | 0.0 |
| Mass Frac | | | | | | | | |
| H2 | 0.000 | 0.003 | 0.000 | 0.000 | 0.000 | 0.000 | 0.000 | 0.000 |
| CO2 | 0.000 | 0.021 | 0.000 | 0.000 | 0.000 | 0.000 | 0.000 | 0.000 |
| CO | 0.000 | 0.008 | 0.000 | 0.000 | 0.000 | 0.000 | 0.000 | 0.000 |
| O2 | 0.000 | 0.001 | 0.000 | 0.000 | 0.000 | 0.000 | 0.000 | 0.000 |
| N2 | 0.000 | 0.034 | 0.000 | 0.000 | 0.000 | 0.000 | 0.000 | 0.000 |
| C1 | 0.001 | 0.056 | 0.000 | 0.000 | 0.000 | 0.000 | 0.000 | 0.000 |
| C2 | 0.002 | 0.079 | 0.000 | 0.000 | 0.000 | 0.000 | 0.000 | 0.000 |
| C2= | 0.000 | 0.000 | 0.000 | 0.000 | 0.000 | 0.000 | 0.000 | 0.000 |
| C3 | 0.000 | 0.008 | 0.000 | 0.000 | 0.000 | 0.000 | 0.000 | 0.000 |
| C3= | 0.000 | 0.000 | 0.000 | 0.000 | 0.000 | 0.000 | 0.000 | 0.000 |
| IC4 | 0.001 | 0.007 | 0.000 | 0.000 | 0.000 | 0.000 | 0.000 | 0.000 |
| NC4 | 0.000 | 0.002 | 0.000 | 0.000 | 0.000 | 0.000 | 0.000 | 0.000 |
| TB2 | 0.000 | 0.000 | 0.000 | 0.000 | 0.000 | 0.000 | 0.000 | 0.000 |
| B-1 | 0.000 | 0.000 | 0.000 | 0.000 | 0.000 | 0.000 | 0.000 | 0.000 |
| IC4= | 0.000 | 0.000 | 0.000 | 0.000 | 0.000 | 0.000 | 0.000 | 0.000 |
| CB2 | 0.000 | 0.000 | 0.000 | 0.000 | 0.000 | 0.000 | 0.000 | 0.000 |
| IC5 | 0.001 | 0.002 | 0.000 | 0.000 | 0.000 | 0.000 | 0.000 | 0.000 |
| NC5 | 0.000 | 0.000 | 0.000 | 0.000 | 0.000 | 0.000 | 0.000 | 0.000 |
| C5-OLE | 0.000 | 0.000 | 0.000 | 0.000 | 0.000 | 0.000 | 0.000 | 0.000 |
| C6-HEA | 0.001 | 0.001 | 0.000 | 0.000 | 0.000 | 0.000 | 0.000 | 0.000 |
| BZ | 0.987 | 0.777 | 0.000 | 0.000 | 0.000 | 0.000 | 0.000 | 0.000 |
| TOL | 0.006 | 0.002 | 0.000 | 0.000 | 0.000 | 0.000 | 0.000 | 0.000 |
| EB | 0.000 | 0.000 | 0.698 | 1.000 | 0.001 | 0.004 | 0.004 | 0.004 |
| IPB | 0.000 | 0.000 | 0.183 | 0.000 | 0.607 | 0.576 | 0.576 | 0.576 |
| DEB | 0.000 | 0.000 | 0.097 | 0.000 | 0.322 | 0.345 | 0.345 | 0.345 |

TABLE 4-continued

| BUTYLBZ | 0.000 | 0.000 | 0.018 | 0.000 | 0.059 | 0.062 | 0.062 | 0.062 |
| PENTYLBZ | 0.000 | 0.000 | 0.004 | 0.000 | 0.012 | 0.013 | 0.013 | 0.013 |
| WATER | 0.000 | 0.000 | 0.000 | 0.000 | 0.000 | 0.000 | 0.000 | 0.000 |

As set forth above, according to exemplary embodiments in the present disclosure, the process for effectively separating and removing by-products (light gas, C5 to C6 hydrocarbon oil fraction, polyethylbenzene) contained in a substantial amount in addition to ethylbenzene as a target compound in the alkylation reaction product of the fluidized catalytic cracking off-gas may be provided to prepare ethylbenzene having high purity. In particular, the fluidized catalytic cracking off-gas, which is not applicable in the conventional process for producing ethylbenzene by using ethylene with high purity, may be used to overcome technical limitations of the technology according to the related art.

In addition, according to an exemplary embodiment in the present disclosure, since ethylbenzene that meets the standards required in the art may be produced, limitation of the conventional ethylbenzene source may be overcome.

Further, according to an exemplary embodiment in the present disclosure, process economical efficiency may be secured by utilizing the polyethylbenzene as an absorbent or gasoline fraction, without requiring a transalkylation reaction for further producing ethylbenzene from polyethylbenzene.

While exemplary embodiments have been shown and described above, it will be apparent to those skilled in the art that modifications and variations could be made without departing from the spirit and scope of the present disclosure as defined by the appended claims.

Detailed Description of Main Elements

F100: HEATING FURNACE  R100: ALKYLATION REACTOR R100
V200: QUENCHER   V201: ABSORPTION TOWER
V202: ABSORBENT RECOVERY COLUMN
V300: BENZENE RECOVERY COLUMN
V301: ETHYLBENZENE RECOVERY COLUMN
100: BENZENE   101: CATALYTIC CRACKING OFF-GAS
102: MIXTURE STREAM   103: PRODUCT STREAM
200: QUENCHER OVERHEAD STREAM
201: ABSORPTION TOWER OVERHEAD STREAM
202: ABSORPTION TOWER BOTTOM STREAM
203: ABSORPTION RECOVERY COLUMN OVERHEAD STREAM
204: SIDE-CUT STREAM
205: ABSORPTION RECOVERY COLUMN BOTTOM STREAM
206: QUENCHER BOTTOM STREAM
207: BENZENE MIXTURE STREAM
300: BENZENE RECOVERY COLUMN OVERHEAD LIQUID STREAM
301: BENZENE RECOVERY COLUMN OVERHEAD VAPOR STREAM
302: BENZENE RECOVERY COLUMN BOTTOM STREAM
303: ETHYLBENZENE
304: ETHYLBENZENE RECOVERY COLUMN BOTTOM STREAM
305: HEAVY OIL   306: GASOLINE POOL
FRACTION STREAM

What is claimed is:

1. A method for recovering ethylbenzene comprising:
reacting a mixture of benzene and fluidized catalytic cracking off-gas comprising ethylene and a light gas in an alkylation reactor to provide a product stream comprising light gas and ethylbenzene;
feeding the product stream to a quencher to separate a quencher overhead stream comprising light gas and a quencher bottom stream comprising benzene and heavier compounds;
feeding the quencher bottom stream to a benzene recovery column to separate a benzene recovery column overhead liquid stream comprising unreacted benzene and a C5-C6 hydrocarbon, a benzene recovery column overhead vapor stream comprising light gas, and a benzene recovery column bottom stream comprising ethylbenzene and heavier compounds; and
feeding the benzene recovery column bottom stream to an ethylbenzene recovery column and recovering ethylbenzene.

2. The method of claim 1, further comprising:
raising a temperature of the benzene or the mixture of benzene and fluidized catalytic cracking off-gas by heat exchange with the product stream.

3. The method of claim 1, wherein the mixture of benzene and fluidized catalytic cracking off-gas is heated and fed to the alkylation reactor.

4. The method of claim 1, further comprising:
feeding the quencher overhead stream to an absorption tower, wherein the quencher overhead stream comprises an amount of heavy oil fraction, absorbing the amount of the heavy oil fraction by an absorbent to be recovered to an absorption tower bottom stream, and mixing the absorption tower bottom stream with the quencher bottom stream.

5. The method of claim 4, wherein the light gas in the quencher overhead stream is recovered to an absorption tower overhead stream.

6. The method of claim 4, wherein the absorption tower bottom stream is fed to an absorbent recovery column to be separated into a side-cut stream comprising benzene and an absorbent recovery column bottom stream, comprising a heavy oil fraction, and the side-cut stream is mixed with the quencher bottom stream.

7. The method of claim 6, wherein at least a portion of the absorbent recovery column bottom stream is fed to the absorption tower as an absorbent.

8. The method of claim 6, wherein the light gas included in the quencher bottom stream fed to the absorbent recovery column is separated into an absorbent recovery column overhead stream and recovered.

9. The method of claim 6, wherein a residue after recovering the ethylbenzene in the ethylbenzene recovery column is discharged into an ethylbenzene recovery column bottom stream, the ethylbenzene recovery column bottom stream is mixed with the absorbent recovery column bottom stream, and at least a portion of a heavy oil fraction stream in which the ethylbenzene recovery column bottom stream and the absorbent recovery column bottom stream are mixed is fed to the absorption tower as the absorbent.

10. The method of claim 4, wherein the benzene recovery column overhead vapor stream is fed to the absorption tower.

11. The method of claim 1, wherein the benzene recovery column overhead liquid stream is recycled to the alkylation reactor.

12. The method of claim 1, wherein the benzene recovery column overhead vapor stream is fed to the absorption tower to absorb benzene with the absorbent, and the absorption tower bottom stream containing the benzene separated from the light gas is discharged from the absorption tower and mixed with the quencher bottom stream.

13. The method of claim 1, wherein a residue after recovering the ethylbenzene in the ethylbenzene recovery column is discharged into an ethylbenzene recovery column bottom stream, and at least a portion of the ethylbenzene recovery column bottom stream is fed to the absorption tower as the absorbent.

* * * * *